United States Patent [19]

Berger et al.

[11] Patent Number: 5,374,722
[45] Date of Patent: Dec. 20, 1994

[54] BRIDGED BENZAZEPINES

[75] Inventors: Joel G. Berger, Cedar Grove; Wei K. Chang, Livingston; John W. Clader, Cranford, all of N.J.

[73] Assignee: Schering Corporation, Kenilworth, N.J.

[21] Appl. No.: 27,167

[22] PCT Filed: Sep. 20, 1991

[86] PCT No.: PCT/US91/06705

§ 371 Date: Mar. 16, 1993

§ 102(e) Date: Mar. 16, 1993

Related U.S. Application Data

[63] Continuation-in-part of Ser. No. 587,894, Sep. 25, 1990, abandoned.

[51] Int. Cl.$^5$ .................. C07D 223/14; C07D 223/16; C07D 223/18
[52] U.S. Cl. .................................................... 540/581
[58] Field of Search .......................... 540/581; 514/217

[56] References Cited

U.S. PATENT DOCUMENTS

| 4,769,368 | 9/1988 | Kaiser et al. | 514/217 |
| 4,957,914 | 9/1990 | Clark et al. | 514/217 |

FOREIGN PATENT DOCUMENTS

| 0233049 | 8/1987 | European Pat. Off. |
| 0285919 | 10/1988 | European Pat. Off. |

OTHER PUBLICATIONS

Weinstock et al. J. Med. Chem., (1987), 30, pp. 1303–1308.
CA 107:58826(t), Weinstock et al (1987).
CA 108:37670(t), Kaiser et al (1987).
Annals of the New York Academy of Sciences, vol. 66, pp. 740–752 (1957), Cook et al.
Clark et al., J. Med. Chem., (1990), 33, pp. 633–641.

*Primary Examiner*—Mukund J. Shah
*Assistant Examiner*—P. I. Datlow
*Attorney, Agent, or Firm*—Eric S. Dicker; Edward Mazer; Matthew Boxer

[57] ABSTRACT

The compound

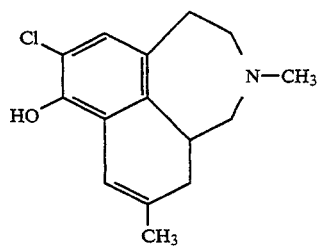

is useful as an agent in the treatment of psychoses and drug dependence and for providing an analgesic effect.

1 Claim, No Drawings

BRIDGED BENZAZEPINES

This application is a continuation in part of U.S. patent application Ser. No. 07/587894, filed Sept. 25, 1990, now abandoned.

BACKGROUND OF THE INVENTION

This invention relates to bridged benzazepines, their preparation and compositions containing them. These compounds are either substituted on the peri-condensed ring or have a GO substituted where G is other than H. These compounds are useful for treatment psychoses.

U.S. Pat. No. 4,957,914 discloses certain bridged benzazepines which are unsubstituted on the peri-condensed ring and lack a GO substituent where G is other than H and G is as described in the present specification.

SUMMARY OF THE INVENTION

The invention relates to compounds of the formula:

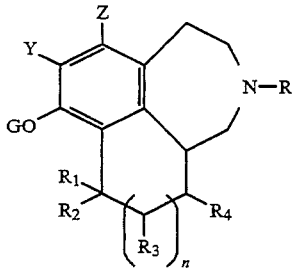

I or a pharmaceutically acceptable salt thereof, wherein

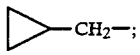

R represents H, alkyl, allyl or
n represents 0 or 1;
$R_1$ and $R_2$ may be the same or different and each independently represents H, OH, $C_1$-$C_4$ alkyl, or Ar with the proviso that $R_1$ and $R_2$ may not both be OH, and with the further proviso that when n is 0, $R_1$ is $C_1$-$C_4$ alkyl or Ar, $R_2$ is $CH_3$ and $R_4$ is H;
$R_3$ and $R_4$ may be the same or different and each independently represents H or $C_1$-$C_4$ alkyl;
G represents H, ($R_5$, $R_6$)NCO— or ArHNCO—;
$R_5$ and $R_6$ may be the same or different and each independently represents H, $C_1$-$C_4$ alkyl, or Ar;
Ar represents phenyl or substituted phenyl;
Y and Z may be the same or different and each independently represents H, halo, $C_1$-$C_4$ alkyl, $C_1$-$C_4$ alkoxy, or $C_1$-$C_4$ haloalkyl.
with the proviso that:
A. at least one of R, $R_2$, $R_3$ and $R_4$ must not be hydrogen; and/or
B. G must represent ArNHCO—, or ($R_5$,$R_6$)NCO— where at least one of $R_5$, $R_6$ represents At.

This invention also includes the compound of the formula

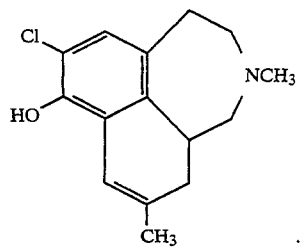

II

Preferred are compounds of formula I wherein n is 1.

Compounds of formula I wherein n is 1 and R is alkyl such as methyl are especially preferred.

Compounds of formula I wherein n i 1. R is methyl and Z is H or chloro are also especially preferred.

Compounds of formula I wherein n is 1, R is methyl and Y is H or chloro are also especially preferred.

Compounds of formula I wherein n as 1, R is methyl, Z is chloro and Y is chloro are also especially preferred.

Compounds of formula I wherean n is 1, R is methyl, Y is $CH_3O$—, HO—, $CH_3$—, or H— are also preferred.

Compounds of formula I wherein n as 1, R is methyl and G is H are still also especially preferred.

Compounds of formula I wherein n is 1, R is methyl and G is ArNHCO— wherein Ar is substituted phenyl are also especially preferred.

As used herein Ph denotes phenyl and i-Pr denotes isopropyl. Also as used herein a broken line ||||denotes a chemical bond below the plane of the page, while a solid line ▶ denotes a chemical bond above the plane of the page. Also as used herein, a squiggly line (∼) denotes a chemical bond whose stereochemistry is not known, or denotes a mixture of compounds wherein one compound has chemical bone of one stereochemistry, and the other compound has the chemical bone of the other stereochemistry The invention also involves pharmaceutical compositions for treating psychoses comprising a compound of formula

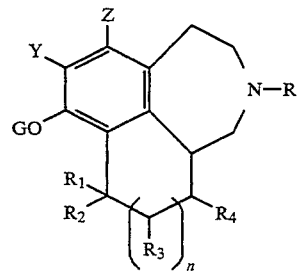

I or a pharmaceutically acceptable salt thereof, wherein

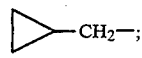

R represents H, alkyl, allyl
n represents 0 or 1;
$R_1$ and $R_2$ may be the same or different and each independently represents H, OH, $C_1$-$C_4$ alkyl or Ar, with the proviso that $R_1$ and $R_2$ may not both be OH, and with the further proviso that when n is 0, $R_1$ is $C_1$-$C_4$ alkyl or Ar, $R_2$ is $CH_3$ and $R_4$ is H;

$R_3$ and $R_4$ may be the same or different and each independently represents H or $C_1$-$C_4$ alkyl;

G represents H, ($R_5$, $R_6$)NCO— or ArNHCO—;

$R_5$ and $R_6$ may be the same or different and each independently represents H, $C_1$-$C_4$ alkyl, or Ar;

Ar represents phenyl or substituted phenyl;

Y and Z may be the same or different and each independently represents H, halo, $C_1$-$C_4$ alkyl, $C_1$-$C_4$ alkoxy, or $C_1C_4$ haloalkyl in combination with a pharmaceutically acceptable carder;

and a pharmaceutical composition for treating psychoses comprising a compound of formula I in combination with a pharmaceutically acceptable carder;

The invention also involves a pharmaceutical composition comprising a compound of formula I or II in combination with a pharmaceutically acceptable carrier and methods for treating drug dependence, for treating a mammal suffering from a D1 dependent neurological disorder, and for providing analgesia in a mammal, which comprise administering to the mammal an effective amount of a compound of formula I or II for such purposes.

DETAILED DESCRIPTION OF THE INVENTION

It is noted that, when $R_1$ and $R_2$ on the same carbon atom are different, e.g., H and $CH_3$, respectively, stereoisomers of the following formulas exist:

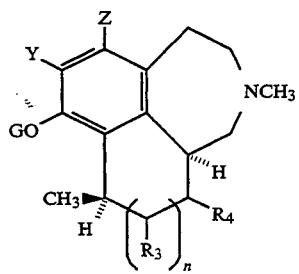

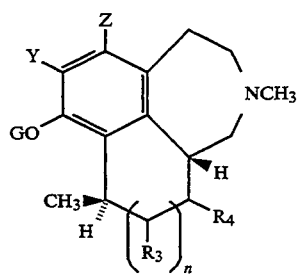

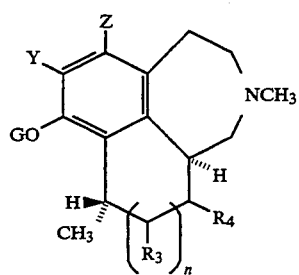

-continued

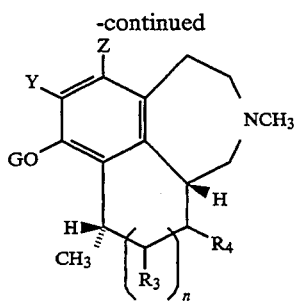

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization or HPLC (high performance liquid chromatography), Compounds of formulas I or II can exist in unsolvated as well as solvated forms, including hydrated forms. In general, the solvated forms, with pharmaceutically acceptable solvents such as water, ethanol and the like are equivalent to the unsolvated forms for purposes of this invention. All such forms are within the scope of this invention.

The compounds of formulas I or II may form pharmaceutically acceptable salts with organic and inorganic acids. Examples of suitable acids for salt formation are hydrochloric, sulfide, phosphoric, acetic, citric, malonic, saliiicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms and are within the scope of this invention.

When utilized herein and in the appended claims, the following terms, unless otherwise specified, have the following meanings:

alkyl (including the alkyl portions of alkoxy, hydroxyalkyi haloalkyl, etc.)- represents a straight or branched, saturated hydrocarbon chain having from 1 to 8. preferably from 1 to 6, carbon atoms (The number of carbon atoms can be designated. For example, $C_1$-$C_4$ alkyl" represents a straight or branched, saturated hydrocarbon having from 1 to 4 carbon atoms.);

alkoxy - represents an alkyl group attached to a molecule through an oxygen atom (alkyl—O—);

allyl - represents the groups —$CH_2$—CH=$CH_2$, —CH=CH—$CH_3$, or—C($CH_3$)=$CH_2$;

halo - represents fluoro, chloro, bromo or iodo;

haloalkyl - represents an alkyi group as defined above wherein 1 to 3 hydrogens thereof have been replaced with a halo moiety, e.g., trifluoromethyl, 2-chloroethyl, etc.; and substituted phenyl - represents a phenyl group in which 1 to 3 hydrogen atoms thereof are replaced by the same or different sustituents independently chosen from hydroxy, alkyl, halo, nitro, alkoxy, haloalkyl including trifluoromethyl, cyano, cycloalkyl, SH, or S(O)pR$^a$[wherein p is 0, 1 or 2 and R$^a$ is alkyl].

As used herein degrees or "°" refers to degrees Celsius unless otherwise indicated.

The compounds of formula I above may be prepared by the methods described below with reference to Schemes 1 and 2, wherein G, Y, Z and R, R$_1$, and R$_2$ are as defined above, unless otherwise indicated:

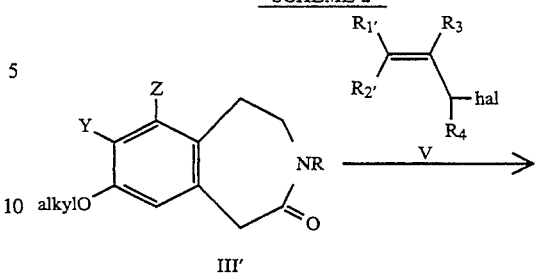

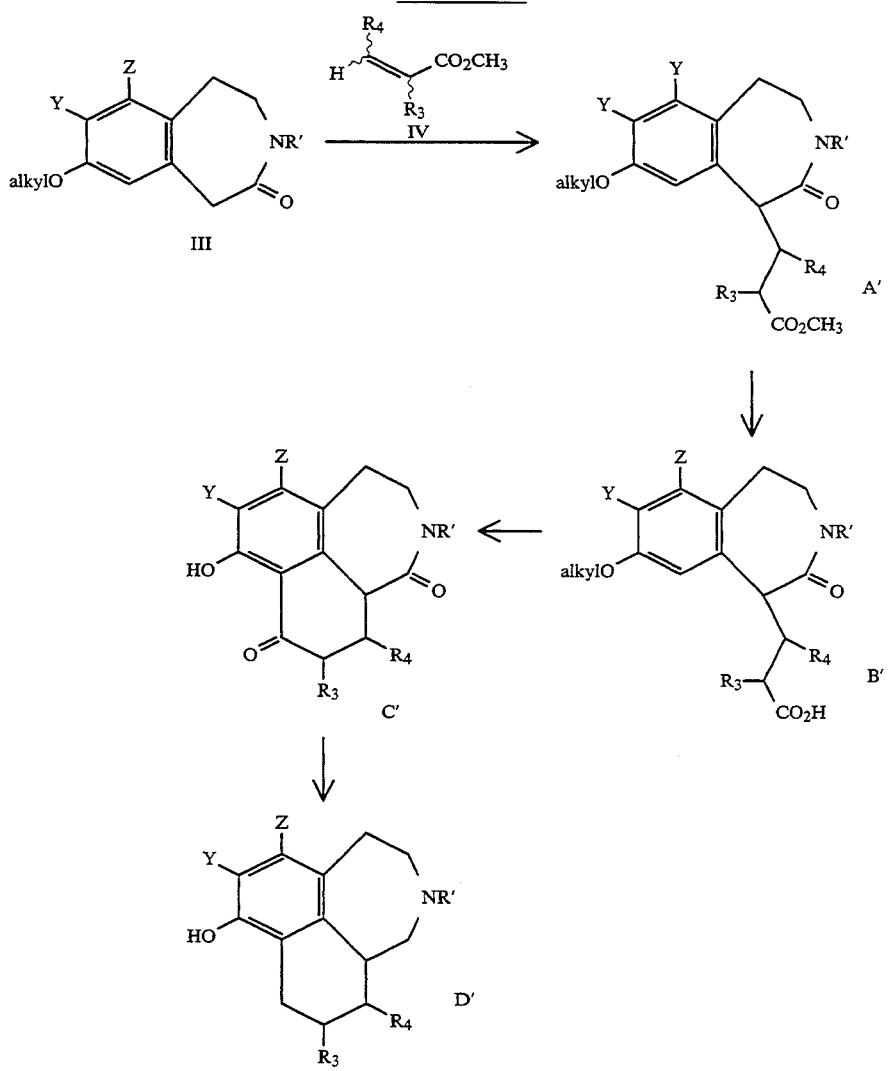

wherein R$_3$, R$_4$, Y and Z are as described above and R' is

H, alkyl or 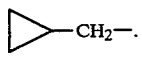

-continued
SCHEME 2
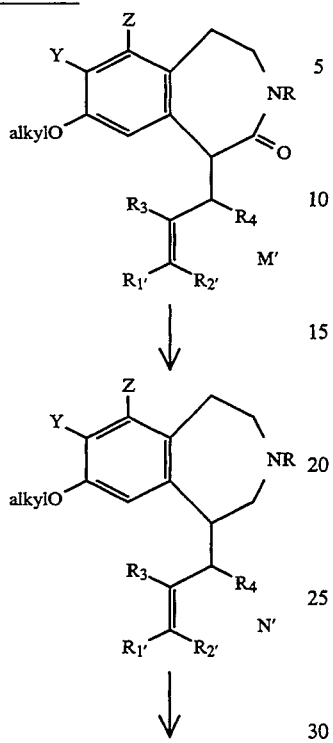
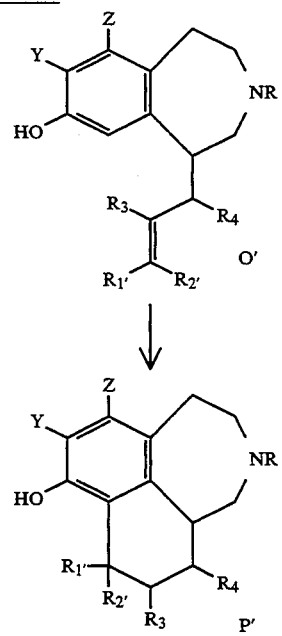
wherein R, R₃, R₄, Y and Z are as described above, and R₁ and R₂ are the same as R₁ and R₂ respectively as previously define, but with the proviso that R₁ and R₂ cannot both be H. Hal is halogen.
SCHEME 3
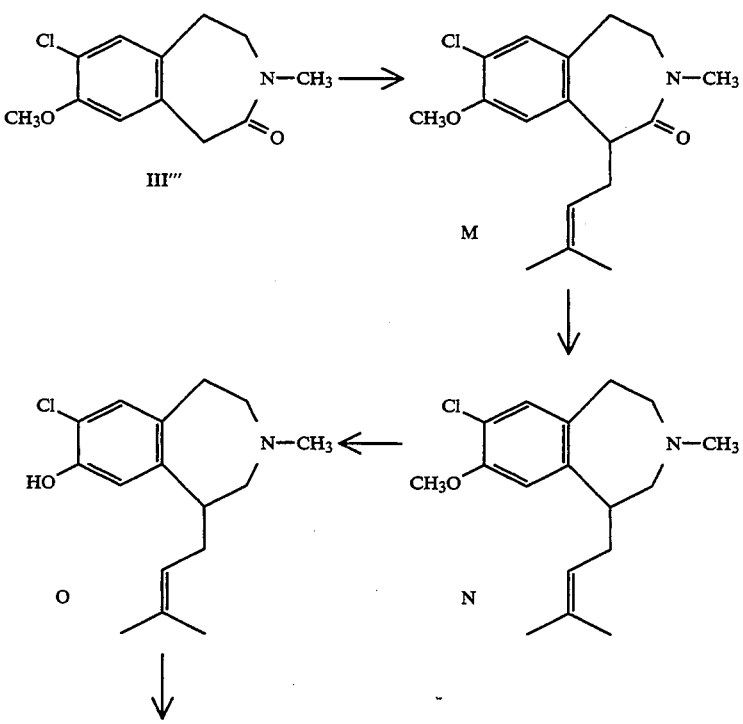

SCHEME 3

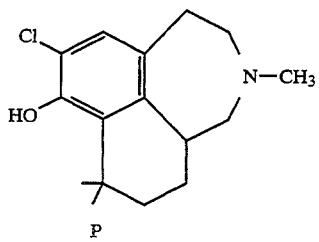

Starting materials of formulas, III, III', III", or III''', are known, or may be prepared as disclosed in EPA 0285,919 or by methods analogous to those disclosed therein. EPA 0285,919 is herein incorporated by reference.

The compounds of formulas IV, V, and VI are known or can be prepared in accordance with known methods In Scheme 1, a compound of formula III may be reacted with a compound of formula IV such as methyl acrylate in a very strong base, preferably, sodium hydride. The reaction is carded out in a polar, aprotic, organic solvent such as dimethylsulfoxide (DMSO). tetrahydrofuran (THF), dimethylformamide (DMF), or more preferably a 9:1 mixture of THF and DMF. The temperature of the reaction is not critical. It can be conducted at about room temperature. The product, a compound of formula A', may be isolated by standard techniques such as adjustment of the pH with an acid, like acetic acid. and extraction.

A compound of formula A' may be hydrolyzed to obtain a compound of formula B', by reaction with a mild base such as $Na_2CO_3$, $Li_2CO_3$, or more preferably potassium carbonate, in a polar, protic. organic solvent such as ethanol. isopropanol or more preferably a mixture of water and methanol at about steam bath temperature. The resulting carboxylic acid of formula B' may be isolated by conventional means such as crystallization.

The resulting carboxylic acid may be isolated and then cyclized to obtain a compound of formula C' by treatment with polyphosphodc acid (PPA) at a temperature of about 72°-80°, preferably about 80°, for about ½ to about 3 hours. The solvent employed for the reaction can be the PPA.

A compound of formula C' may be reduced by reaction with a reducing agent such as lithium aluminum hyde (LAH), or more preferably $BH_3$ in an organic solvent such as ether, diglyme or more preferably THF. The reaction may be conducted at the reflux temperature of the solvent employed. The reaction may be carried out for a pedod of about ½ to about 4 hours. Isolation of a compound of formula D' may be conventional means.

In Scheme 2, a compound of formula M' may be prepared by reacting a compound of formula III' with a halogenated olefin of formula V in the presence of a strong base such as lithium diisopropylamide (LDA), or more preferably Nail. In a polar organic solvent such as DMSO. or more preferably a mixture of DME and DMF. The reaction is conducted at a temperature in the range of about −78° to about 30°, preferably at about room temperature. The resulting compound of formula M' may be isolated by conventional techniques such as crystallization.

A compound of formula M' may be reduced to obtain a compound of formula N', by treatment with a reducing agent such as LAH, in a dry, polar, organic solvent, like diethyl ether, or more preferably THF, at temperature starting at about 50° with gradual, cooling to about 40°. The resulting reduced compound of formula N' may be isolated by conventional means such as column chromatography.

A compound of formula N' may be convened to the corresponding hydroxy compound of formula O' by treatment with a strong base such as KH, or more preferably Nail, and a mercaptan, such as butyl-SH, or more preferably ethanethiol in a polar, aprotic organic solvent such as DMSO, or more preferably DMF, under an inert atmosphere such as argon or more preferably nitrogen, at a temperature of from about 100° to about 150° for about 2 hours to about 5 hours. The resulting compound of formula O' may be isolated by conventional means.

A compound of formula O' may be cyclized to a compound of formula P' by treatment with an organic acid, such as $CF_3CO_2H$, paratoluene sulfonic acid, or more preferably $CH_3SO_3H$ at a temperature of from about 0° to 50° for about 2 hours. The resulting cyclized compound of formula P' may be isolated by conventional techniques such as neutralization of the resulting reaction mixture followed by recrystallization.

The conversion of the compound of formula III''' in Scheme 3, into compounds M, N, O and finally P is described in the examples below.

A compound of formula I or II may be convened to its corresponding acid addition salt, such as its hydrochloride salt, by treatment with HCl. Typically, a compound of formula I or II will be dissolved in a polar organic solvent, such as methanol, or more preferably a mixture of $CH_2Cl_2$ and EtOH. To this solution will be ethereal HCl, and the resulting hydrochloride salt will be recovered by recrystallization and drying.

A compound of formula I' below may be convened to a compound of formula I below by conventional means.

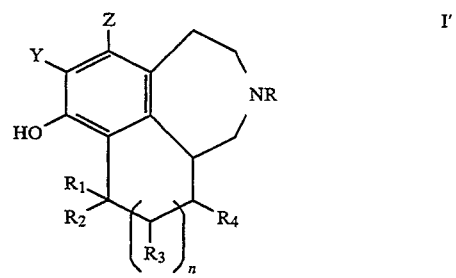

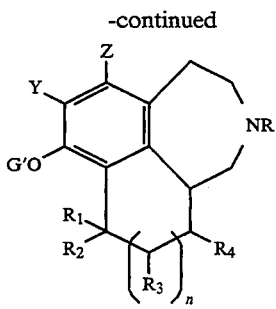

wherein R, $R_1$, $R_2$, $R_3$, $R_4$, Z, Y, and n are as described above; and G' corresponds to G with the proviso that it cannot be H.

The reaction is carded out by treating a compound of formula I' with an appropriate isocyanate so as to achieve a compound of formula I'' with the desired group G'. Isocyanates required to cover the full range of values for G' are either known or can be prepared by known means.

For example, the compound of formula D from example 2(I) may be convened to the compound of formula D'' from example 2(I ) by reaction with 4-isopropylphenyl isocyanate in an aprotic, organic solvent such as $CH_2Cl_2$, $CHCl_3$ or more preferably toluene, at the reflux temperature of the solvent employed for a period of about ½ to about 3 hours followed by cooling to room temperature. The resulting product may be isolated by conventional techniques such as evaporation of the reaction mixture followed by titration and drying. This reaction is described more specifically in Example 2(I) below.

The compounds of formula D', P', Q'', and P which are compounds of formula I' may be similarly convened to compounds of formula I'' of the invention. Indeed, as noted above, any compound of formula I' may be converted to a corresponding compound of formula I''. It will be appreciated that compounds of formulas I' and II'' are encompassed by formula I of the invention.

A compound of formula I''',

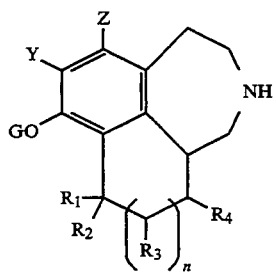

wherein $R_1$, $R_2$, $R_3$, $R_4$, G, Y, Z and n are as described above, may, be convened to a corresponding N-allyl compound of formula

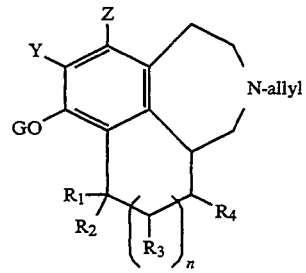

by conventional means such as treatment with an allyl bromide compound. It will be appreciated that a compound of formula D' above, wherein R' is H may be similarly convened to a corresponding N-allyl compound. Compounds of formulas I''', $I^{IV}$, D' and N-allyl compounds corresponding to compounds of formula D' are encompassed by formula I of the invention.

The compounds of formula I or II of the invention are useful as agents for treating psychoses, drug dependence, D1 dependent neurological disorders, and for providing analgesia.

The antipsychotic activity of the compounds of the invention may be demonstrated in the following protocol.

CONDITIONED AVOIDANCE SUPPRESSION IN RATS

Clinically active antipsychotic drugs are known to depress discrete trial avoidance behavior at doses that do not retard escape response (Ann. N. Y. Acad. Sci. 66, 740 (1957)). A sedes of experiments was carried out to assess the ability of the compounds of this invention to suppress the conditioned avoidance response (CAR) in rats.

MATERIALS AND METHODS

Rats were required to jump onto a platform located 6.75 inches (17.15 cm) above the odd floor of an experimental chamber in response to a 5-second tone to avoid a 10-second foot shock (0.6 mA). Each experimental session consisted of 20 such trials presented at second intervals. A correct CAR is scored whenever the rat jumps onto the platform during the tone (odor to foot shock). An escape response is scored when the rat jumps onto the platform during a shock. A response failure is defined as the lack of an escape response during the 10-second shock period.

Groups of 6-8 rats were trained in two consecutive days (total of 40 trials). By day 2, rats that achieved correct CARs on 16 or more of the 20 trials were treated with either a test drug or vehicle on day 3. Suppression of CAR was analyzed statistically using the Students-test comparing the performances of drug-treated to vehicle treated rats. The minimal effective dose (MED) for each drug is defined as the lowest dose tested that significantly ($P \leq 0.05$) reduced avoidance responding.

COMPETITIVE INHIBITION ASSAY

Many compounds capable of effecting reproducible physiological changes in neural tissues are believed to operate by binding at one or more receptor sites. Compounds which interact strongly with these receptor sites in in vitro tests, using homogenates of the target organ or structure, are expected to exhibit similar properties when administered in vivo and are, therefore, therapeutic and/or diagnostic agents.

Binding of a compound to a receptor site, in vitro, is demonstrated by the specificity of binding and the saturability of the available sites. A methodology for characterization of D-1 and D-2 receptor binding and an interpretation of the data are described by Billard et. al., Life Sciences 35, 1885 (1984) in which the binding of the benzazepine (R)-(+)-8-chloro-2,3,4,5-tetrahydro-3-methyl-5-phenyl-1H-3-benzazepin-7-ol hemimaleate, Compound B" to the dopamine D-1 receptor is characterized, A selectivity for D-1 receptor binding as compared to D-2 receptor binding is believed to confer the therapeutic advantage of avoiding troublesome and potentially irreversible neurological side effects associated with D-2 receptor occupancy.

MATERIALS AND METHODS

Tritiated compound B and tritiated spiperone (a potent D-2 receptor ligand) are obtained as described in the Billard et al. reference supra and sedaity diluted in 0.05 M Tris buffer, pH 7.4, as required, Compounds of this invention are synthesized as disclosed herein and diluted in 0.05 M Tds buffer, pH 7.4, as required,

TISSUE PREPARATION

Male Sprague-Dawley rats (200 to 250 g) from Charles River Breeding Laboratories, Mass. are used to obtain brain tissue. The rats are humanely sacrificed and their brains removed and placed on ice. Stdatal tissue is excised, pooled, and homogenized (Brinkman Polytron, 10 sec) in 100 volumes (w/v) of ice cold 50 mM Tds buffer, pH 7.4 (at 25° C). The homogenate is centrifuged at 20,000 xg for 10 min. The resultant pellet is rehomogenized in Tds buffer and centrifuged again. The final pellet is resuspended in 50 mM Tds buffer pH 7.4 containing 120 mM NaCl, 5 mM KCI, 2 mM $CaCl_2$, and 1 mM $MgCl_2$.

ASSAY

Polypropylene incubation tubes receive 100 μof the individual test compounds at vanous concentrations dissolved or suspended in 0.05 M Tris, pH 7.4 containing 4 mg/ml methylcellulose, 100 μl of a solution of tritiated compound B in Tds buffer (final reaction mixture concentration =0.3 nM) or 100 μl Of a solution of $^3H$-spiperone in Tris buffer (final concentration =,0.2 nM) and 800 tl of tissue suspension (ca. 3 mg/assay). Tubes are incubated at 37° C. for 15 minutes and rapidly vacuum filtered through Whatman GF/B filters and dosed 4 times with 4 ml of ice cold 50 mM Tris buffer, pH 7.4. The filters are transferred to scintillation vials, equilibrated with 10 ml of scintillant (Scintosol, Isolab, Inc.) for 16 hours at 25° C. and the radioactivity determined in a liquid scintillation counter. $K_i$ values are determined as described by Billard et al. using the relationship $K_i = LC_{50}/(1+([L]/K_D))$ wherein $IC_{50}$=concentration of test drug necessary to displace 50% of specifically bound titrated compound B', [L] =concentration of radioligand used in the assay, and $K_D$=dissociation constant. Ki values for the displacement of compound B*, and Ki values for the displacement of spiperone were determined and are shown in Table I below. The unit for such Ki values is nanomolar (nM).

RESULTS

The inhibition constants (Ki) determined from the assays for a series of compounds of the invention are as shown in Table 1 below.

TABLE 1

Biological Activity of Compounds of Formula I

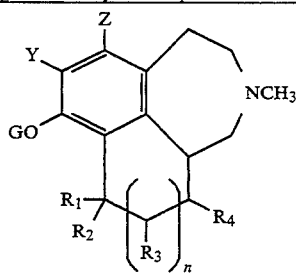

| Y | Z | n | G | R1 | R2 | R3 | R4 | $K_i$ Compound B* Displacement | $K_i$ Spiperone Displacement | Rat CAR MED*- Oral | Rat CAR MED* sc | mp HCl |
|---|---|---|---|----|----|----|----|----|----|----|----|----|
| Cl | H | 1 | H | H | H | H | H | 6.2 | 500 | >30 | 0.3 | >250 |
| Cl | H | 1 | Me2NCO | H | H | H | H | 1006 | 8009 | 10 | 3 | 236-9 |
| Cl | H | 1 | H | C6H5 | H | H | H | 2080 | 42800 | >30 | >10 | 223-5[a] |
| Cl | H | 1 | H | CH3 | CH3 | H | H | 256 | 218 | <30 | >10 | 217-9[a] |
| Cl | H | 1 | H | HO | H | H | H | 110 | 6593 | | | 153-4 |
| Cl | H | 0 | H | CH3 | CH3 | H | H | 65 | 147 | ≈30 | 3.0 | 162-4[a] |
| Cl | H | 1 | H | CH3 | H | H | H | 42 | 248 | 3 | 0.1 | 194-6[a] |
| Cl | H | 1 | H | H | CH3 | H | H | 51 | 389 | | | 179-81[a] |
| CH | H | 1 | H | H | H | H | H | 350 | 3350 | | | 265-70 |
| CH3 | H | 1 | H | H | H | H | H | 37 | 1300 | ≦30 | | 275-280 |
| Cl | Cl | 1 | H | H | H | H | H | 1.1 | 230 | 10 | | 275-8 |
| Cl | H | 1 | 4-i-PrPhNHCO | H | H | H | H | 51 | 680 | ≦30 | | 152-3 |
| Cl | H | 1 | 3,5-(MeO)2Ph—NHCO | H | H | H | H | 6.6 | 405 | 10 | | 214-6 |
| H | H | 1 | 4-iPrPhNHCO | CH3 | H | H | H | 134 | 420 | >30 | | 175-8 |
| H | H | 1 | 3,5-(MeO)2Ph—NHCO | CH3 | H | H | H | 35 | 337 | >30 | | 199-201 |
| Cl | H | 1 | H | H | — | CH3 | — | 32 | 264 | >30 | | 154-6 |
| Cl | H | 1 | H | H | H | CH3 A/B 2:1 | H | 4.5 | 250 | | | 132-7[a] |

TABLE 1-continued

Biological Activity of Compounds of Formula I

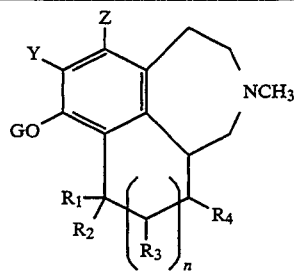

| Y | Z | n | G | $R_1$ | $R_2$ | $R_3$ | $R_4$ | $K_i$ Compound B* Displacement | $K_i$ Spiperone Displacement | Rat CAR MED*- Oral | Rat CAR MED* sc | mp HCl |
|---|---|---|---|---|---|---|---|---|---|---|---|---|
| Cl | H | 1 | H | H | H | H | $CH_3$ | | | | | 270–3 |

$K_i$ Compound B* displacement is described above.
$K_i$ Spiperone displacement is described above. nM is nanomolar.
Rat Car MED = minimal effective dose in rats in the conditioned avoidance response suppression test at 1 hr. post-treatment after oral and 0.5 hr. after subcutaneous (sc) administration.
mp HCl means melting point in degrees Celsius of the hydrochloride salt.
$^a$is a free base
*Where $R_2$ and $R_4$ are both — there is a carbon—carbon bond.

The comparatively small Kt values of the compounds of the invention in the competitive binding assay with compound B* indicate that the compounds of formula I bind strongly to the D-1 receptor site. The relatively high Ki values for the D-2 site. for which spiperone is highly selective, indicate that the compounds are not specifically bound to that receptor site.

Selective activity for D1 receptors is indicative of these compounds' potential use as D1 antagonists in treating disorders that may be lessened by D1 antagonists as discussed in Beaulieu. Canadian J. Neur. Sci. 14(3):402 (1987) and Waddington, Gen. Pharmac. 19(1):55 (1988). These disorders include disorders associated with stereotypic behaviors and drug dependence. D1 antagonists have been shown to block cocaine- and morphineI dependent pleasure sensations making the compounds of the present invention useful in treating drug dependence. Furthermore, although the precise mechanisms involved in a variety of movement disorders are unknown, it is generally accepted that they all use the striatum as a final common pathway. The striatum contains the highest density of D1 receptors suggesting that movement disorders may be treated using D1 antagonists. Consequently, the compounds of the present invention have potential utility in treating movement disorders such as Parkinson's disease, Huntington is chorea and tardive dyskinesias. Additionally, antagonists have potential utility as inhibitors of disorders associated with repetitive, stereotypic behavior such as Lesch-Nyhan disease.

The antidepressive method of the invention may be demonstrated, for example, by test procedures which measure a compound's effect on tetrabenazine (TBZ)-induced ptosis in mice or which measure a compound's effect on muricide activity in rats as discussed below.

ANTIDEPRESSANT POTENTIAL

EFFECTS ON TETRABENAZINE (TBZ-INDUCED PTOSIS IN MICE

Clinically active antidepressant drugs are known to block TBZ-induced ptosis in mice (Psychosomatic Medicine, Nodine and Moyer, Eds., Lea and Febiger, Philadelphia, 1962, pp 683–90). Activity in this test is used to predict anti-depressant activity in man.

METHODS AND MATERIALS

Groups of 5 mice are administered test drugs followed 30 minutes later by intrapedtoneal (ip) injection of tetra-benazine, 30 mg/kg. Thirty minutes later, the degree of ptosis is evaluated. Percent blockade of each treated group is used to determine $ED_{50}$'s defined as that dose which prevents ptosis in 50% of mice. $ED_{50}$'s and 95% confidence limits are calculated by probit analysis.

EFFECTS ON MURICIDAL BEHAVIOR IN RATS

Blockade of mudcidai (mouse-killing) behavior in rats is used as a measure of evaluating the anti-depressant activity of drugs (Int. J. Neuro-pharmacol., 5. 405–11 (1966)).

METHODS AND MATERIALS

Groups of 5 rats are administered test drug intrapedtoneally and are tested 30 and 60 minutes later for presence of mudcidai behavior. Percent blockade of each treated group using data obtained at both these time points is calculated and dose-response data are used to determine each $ED_{50}$. $ED_{50}$ is defined as that dose which blocks mudcide behavior in 50% of treated rats and is calculated using probit analysis.

The analgesic effect of the compounds of formula I and the method for providing analgesia may be exemplified by the Acetic Acid Writhing Test in mice described below.

ACETIC ACID WRITHING TEST IN MICE

The blockade of writhing induced by the intraperitoneal injection of acetic acid is an established experimental animal model for the screening of antinociceptive drugs (drugs which prevent the appreciation or transmission of pain sensations). See Hendershot et. al., Pharmacol. Exp. Therap. 125:237, (1959) and Koster et. al., Fed. Proc. 18:412, (1959).

METHODS AND MATERIALS

Compounds to be tested are dissolved or suspended in aqueous 0.4% methylcellulose vehicle. For oral administration, dosages are prepared for delivery of the selected weight of compound a total volume of 20 mg/kg of body weight. For subcutaneous or intraperitoneal administration, dosages are prepared for delivery of the selected weight of compound in a volume of 10 ml/kg of body weight.

The test procedure is that described by Hendershot et. al., supra, except that acetic acid is substituted for phenylqui none. Groups of five male CF1 mice (20–26 g.) are dosed orally with test drug and injected 15 minutes later with 0.6 ml aqueous acetic acid (10 mg/kg). The mice are placed in a large observation beaker and the number of writhes for each animal is counted dudng a 10 minute interval starting 3 minutes after injection of acetic acid. A writhe is defined as a sequence of arching of the back, pelvic rotation and hindlimb extension. Initial screening is performed using a dosage of 30 mg/kg. If this dose affords 50% or greater reduction in the number of writhes compared to the control, the animal is considered to be protected, a dose response curve is developed using a logarithmic sequence of lower doses and an ED5o is determined by interpolation.

The compounds of the invention are selective D1 receptor antagonists. D 1 antagonists have been shown to block cocaine- and morphine-dependent pleasure sensations making the compounds of the present invention useful in treating drug dependence. The activity of the compounds of the invention in treating drug dependence may be demonstrated by the protocol described in Kleven, et al., *Psychopharmacology* (1988) 95: pp. 427–429 or by the procedure described in Koob, et. al., *Neuroscience Letters.* 79 (1987) pp. 315–320.

The compounds can be administered orally, topically, parenteraily, or by oral or intranasal inhalation. The preferred mode of administration is orally or intravenously.

The compounds can be administered in conventional oral dosage forms such as capsules, tablets, pills, powders, suspensions or solutions prepared with conventional pharmaceutically acceptable excipients and additives, using conventional techniques. Parenteral preparations, i.e., sterile solutions or suspensions are also made by conventional means. Inhalation administration can be in the form of a nasal or oral spray. Insufflation is also contemplated.

For preparing pharmaceutical compositions from the compounds described by this invention, inert, pharmaceutically acceptable carders can be either solid or liquid. Solid form preparations include powders, tablets, dispersible granules, capsules, cachets and suppositories. The powders and tablets may compdse from about 5 to about 70 percent active ingredient. Suitable solid carders are known in the art, e.g., magnesium carbonate, magnesium stearate, talc, sugar, lactose. Tablets, powders,-cachets and capsules can be used as solid dosage forms suitable for oral administration.

Liquid form preparations include solutions, suspensions and emulsions. As an example may be mentioned water or waterpropylene glycol solutions for parenteral injection.

Liquid form preparation may also include solutions for intranasal administration.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be convened to liquid form may contain in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

For prepanng suppositories, a low melting wax such as mixture of fatty acid glyceddes or cocoa butter is first melted, and the active ingredient is dispersed homogeneously therein as by stirring. The molten homogeneous mixture is then poured into conveniently sized molds, allowed to cool and thereby solidify.

Preferably, the pharmaceutical preparation is in unit dosage form. in such form, the preparation is subdivided into unit doses containing appropriate quantities of the active component, e.g., an effective amount to achieve the desired purpose.

When used orally, the compounds of the invention can be administered to a mammal in need of such treatment in an amount ranging from about 0.01 mg/kg body weight to about 30.0 mg/kg body weight. When used parenterally, the compounds of the invention can be administered in a range of about preferably from about 0.001 mg/kg body weight to about 10.0 mg/kg body weight per day.

Determination of the proper dosage of a compound of the invention for a particular situation is within the skill of the art. Generally, treatment is initiated with smaller dosages that are less than the optimum dose of the compound, Thereafter, the dosage is increased by small increments until the optimum effect under the circumstances is reached. For convenience, the total daily dosage may be divided and administered in portions during the day if desired.

The amount and frequency of administration of the compounds of formula [and the pharmaceutically acceptable salts thereof will be regulated according to the judgment of the attending clinicjan considering such factors as age, condition and size of the patient as well as sevedty of the symptom being treated.

The invention disclosed herein is exemplified by the following preparative examples, which should not be construed to limit the scope of the disclosure. Alternative mechanistic pathways and analogous structures within the scope of the invention may be apparent to those skilled in the art.

EXAMPLE 1

Preparation of 6⊖-Chloro-2-Methyl-1.2.3.4.8.9.10.10a-octahydro-naphth [1.8-cd]azepin-7-ol.

A. 3-(7-chloro-8-methoxy-3-methyl-2-oxo-2,3,4,5-thetrhydro-1H-3-benzazepin-1-yl) propionic acid, methyl ester.

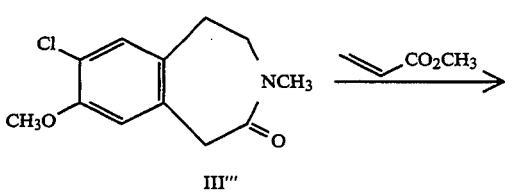

III''''

A 60% suspension of NaH in mineral oil (0.06 mole) was adried portionwise with cooling and stirring to a solution of the starting material III'''' ( 14.4 g, 0.06 mole) in 120 ml of a 9:1 mixture of tetrahydrofuran (THF)/dimethylformamide (DMF). The resulting mixture was stirred for 20 minutes, and a solution of methyl acrylate (0.06 mole) in 10 ml of THF adried dropwise with stirring. After stirring for an additional 2 hrs, 15 ml of water was adried dropwise with cooling and stirring. After frothing had subsided, the reaction mixture was diluted with 350 ml of water, and the pH adjusted to ~5 with acetic acid. The mixture was extracted with 200 ml of ether foilorbed by 100 ml of methylene chloride. The combined extracts were dried over Mg. SO4, and evaporated in vacuo. The residue was triturated with cold ether, and the solid product filtered and dried to give 7.95 g of product, mp 95°–97°.

B. 3-(7-chloro-8-methoxy-3-methyl-2-oxo-2,3,4,5-tetrahydro-1H-3-benzazepin-1-yl) propionic acid.

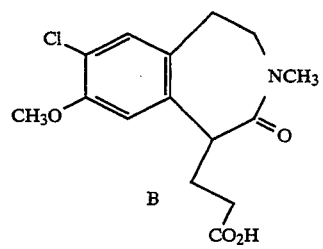

A mixture of 15.0 g of K2CO3, 80 ml of water, 120 ml of methanol, and 7.95 g of product A above was heated on the steambath for 2 hrs. The resulting mixture was the concentrated to ca. 100 ml, diluted with 150 ml of water, chilled, and extracted with 100 ml of ether. The aqueous layer was separated, cooled, and acidified with concentrated HCl. The precipitated solids were filtered off, washed with water, and allowed to dry in air overnight to give 7.25 g of product.

C. 6-Chloro-1,8-diketo-2-Methyl-1,2,3,4,8.9,10,10a-octahydro-naphth [1,8-cd]azepin-7ol.

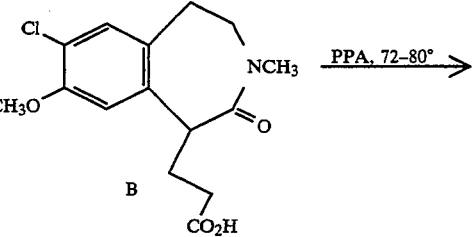

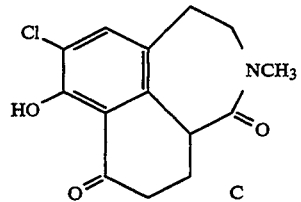

A mixture of 6.75 g of the preceding product B in 70 g of polyphosphodc acid was heated in an oil bath at 72°–80° with stirring for 45 min. The mixture was then poured over 600 ml of ice-water with stirring. After 15 minutes of stirring, the mixture was extracted with two 100 ml portions of methylene chloride. The combined extracts were filtered through Celite, then dried over MgSO4. After filtration of the drying agent, the filtrate was evaporated to dryness to give a viscous syrup which was crystallized from 20 ml of ethyl acetate thus yielding 3.9 g of product C, mp 140°–142° .

D. 6-Chloro-2-Methyl-1,2,3,4,8,9, 10, 10a-octahydro-naphth [1,8-cd]azepin-7-ol.

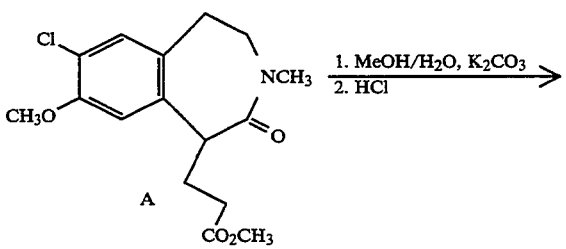

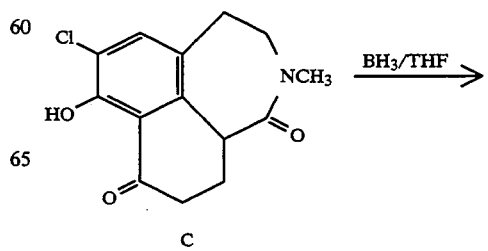

-continued

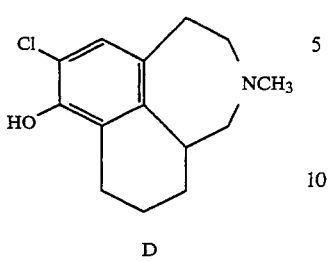

D

A solution of 3.9 g of product C above in 20 ml of THF was treated with 50 ml of 1 M BH₃ in THF. The resulting mixture was heated at reflux for 6.5 hrs,, then allowed to stand at room temperature overnight, The mixture was concentrated to about, 20 ml, and then treated dropwise with cooling with 20 ml of ethanol followed by 50 ml of 4 N HCl. This mixture was then heated on the steambath with stirring for 30 rain, diluted with 100 ml of water, and adjusted to pH~8 by dropwise addition of 50% NaOH. Precipitated material was filtered off, washed with cold water, and air dried overnight yielding 2.6 g of product.

The aqueous flitrates were extracted with 50 ml of CH2Cl2, and the extract evaporated to give ca. 300 mg of oily residue. The solid product was recrystallized from 180 ml of CH₃CN/EtOH (1:2) to give 1.85 g of hydrochloride salt of D, mp 277°–280°. This material was dissolved in 120 ml of boiling water, the solution treated with solid NaHCO₃ to pH~8, the solution chilled, and the precipitated solids filtered giving 1.45 g or free base. This material was chromatographed over 150 g of thin-layer chromatography grade silica gel eluting with CHCl₃/EtOH/NH₄OH (50:3:1). Fractions which were homogeneous by TLC were combined and evaporated, and the residue dried in vacuo at 90 o for 4 hrs to yield 1.0 g of product D, mp 177°–178°..

EXAMPLE 2

Preparation of
5.6-Dichloro-2-Methyl-1.2.3.4.8.9.10/10a-octahydro-naphth [1,8-cdπazepin-7-ol.

E. 7-Methoxy-2-Methyl-1-Oxo-1,2,3,4,8,9,10,10a-octaghydro-naphth [1,8-cd]azepine.

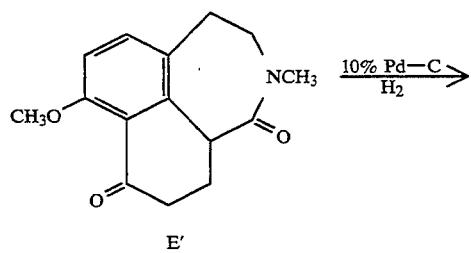

E'

-continued

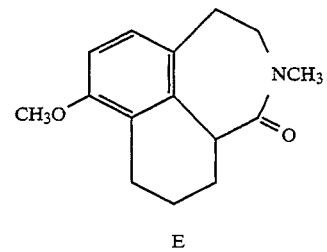

E

A suspension of 20.0 g of E' in 350 ml of EtOH and 10 ml of conc. HCI was hydrogenated over 2.2 g of 10% Pd on carbon at 20–25 pounds per square inch gage (psig) for 24 hrs. Catalyst was filtered;/ and solvent evaporated to give 18.0 g of solid product E. Compound E' was prepared in a manner similar to the preparation of compound C in Example 1 (C) above.

F. 7-Methoxy-2-Methyl-1,2,3,4,8,9,10,10a-octahydro-naphth[1,8-cd]azepine.

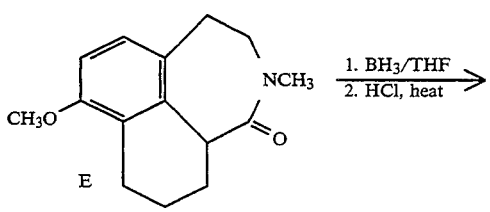

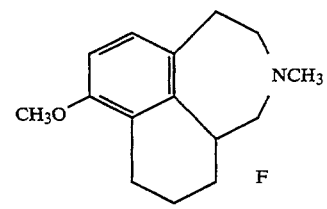

F

A solution of 18.0 g of product E in 200 ml of THF was treated with 145 ml of 1 M BH₃ in THF dropwise with cooling and stirring. The reaction mixture was then heated at reflux with stirring overnight. The resulting mixture was reduced to dryness at slightly reduced pressure, and the residue then treated by dropwise addition of 100 ml of ethanol with cooling and stirring followed by 70 ml of 20% HCI. After heating at reflux for 2 hrs, most of the solvent was removed in vacuo, the residue diluted with 300 ml of water, and the solution rendered basic with 50% NaOH. The resulting mixture was extracted with two 200 rnl of ether, the combined extracts dried over MgSO₄, filtered, and the filtrate evaporated to dryness to give 15.3 g of product F as a viscous syrup.

G. 5,6-Dichloro-7-Methoxy-2-Methyl-1,2,3,4,8,9,10,10a-octahydro-naphth[1,8-cd]azepine.

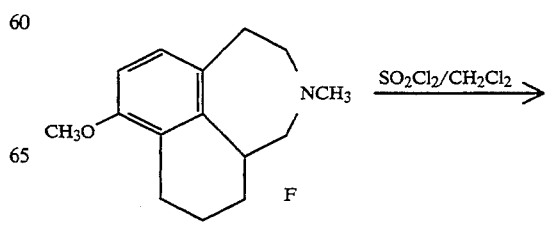

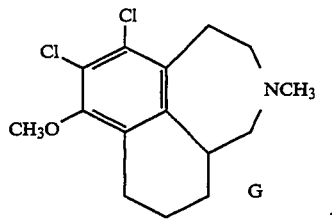

A solution of product F (15.0 g) in 300 ml of CH$_2$Cl$_2$ was treated by dropwise addition of 160 ml of a I M solution of SO$_2$Cl$_2$ in CH$_2$Cl$_2$ with cooling and stirring in an ice bath. Stirring was continued for 1 hr in the ice bath, then at room temperature overnight. The reaction mixture was then cooled in ice and treated by slow addition of a 5% solution of K$_2$CO$_3$ with stirring until pH 8 was reached. The organic layer was then separated, dried over MgSO$_4$, filtered, and evaporated to dryness to give ~19 g of a dark viscous syrup. This material was taken up in 40 ml of CH$_2$Cl$_2$ and chromatographed over 600 g of thin layer chromatography (tlc) grade silica gel eluting with CH$_2$Cl$_2$/EtOH/NH$_4$OH (100:3:1). Fractions containing the desired product, as determined by tlc, were combined, and evaporated to dryness giving 2.9 g of viscous syrup G.

H. 5,6-Dichloro-2-Methyl-1,2,3,4,8,9, 10,10a-octahydronapth[1,8-cd]azepin-7-ol

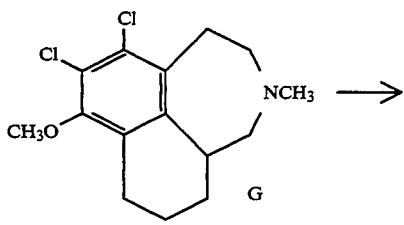

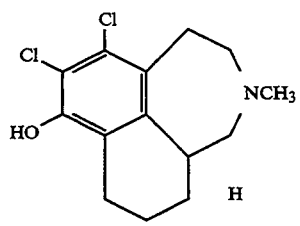

Product G was dissolved in 50 ml of EtOH and filtered to remove a small amount of insoluble material. The filtrate was evaporated to dryness, the residue treated with 30 ml of 48% HBr, and the mixture then stirred and heated in an oil bath at 1300 for 6 hrs. The mixture was then reduced to a volume of ~15 ml under reduced pressure, and the residue dissolved in 600 ml of boiling water. The hot mixture was treated portionwise with solid NaHCO$_3$ to pH~8, and allowed to stand at room temperature overnight.

The precipitated dark solids were filtered and washed with water. The filtrates were extracted with 150 ml of CH$_2$Cl$_2$ and the extracts and solids combined. The resulting solution was dried over MgSO$_4$, filtered, and treated with excess ethereal HCl. The mixture was then evaporated to dryness, and the residue digested with 60 ml of ethyl acetate/ethanol (3:1) on the steam bath. After cooling, the solids were filtered and dried at 90° in vacuO for 5 hrs to give 2.1 g of product H mp 275°–278°.

I. Prepartoin of b 6-Chloro-7-[(4-Isoporpyl-phenylamino) Carbonyloxy]-2-Methyl-1,2,3,4,8,9,10,10a-Octahydro-Naphth]1,8-cd]azepine, hydrochloride.

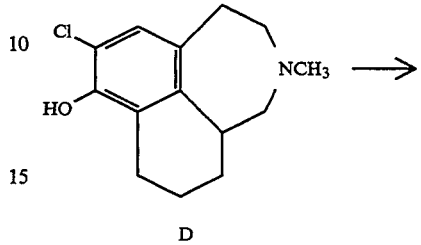

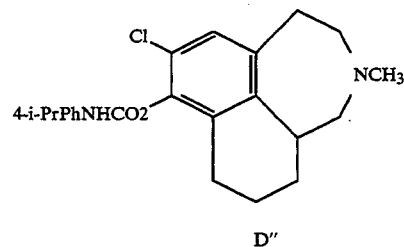

4-isopropylphenyl isocyanate (0.33 g., 2.0 mmol) was adried to a suspension of compound D (0.3 g, 1.2 retool) in 30 ml of toluene, and the mixture heated at reflux for 4.5 hrs. The reaction mixture was then cooled to room temperature, and stirred overnight under nitrogen. Evaporation of solvent in vacuo left an oil, which was dissolved in ether and treated with ethereal HCl. A small amount of ethanol was adried to the suspension, and the mixture evaporated to dryness. The resulting solid was triturated with acetonitrile, filtered, and dried in vacuo to give 0.49 g of product mp 152°–153°.

J. Preparation of 2-Methyl-1,2,3,4,8,9, 10,10a-OctahydroNaphth[1,8-cd]azepine-7-ol.

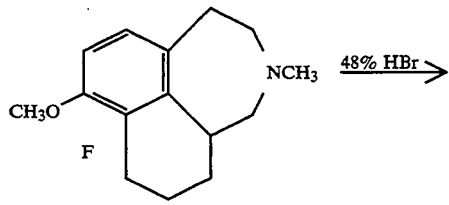

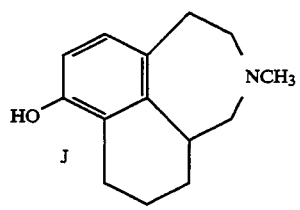

A solution of compound F (27 g) in 250 ml of 48% HBr was heated in an oil bath at 125°–130° with stirring for 6.5 hrs. The mixture I 0 was then chilled in an ice bath, and the precipitated solids filtered and washed with cold water. The wet solids were then dissolved in 75 ml of dimethyiformamide (DMF) with heating, and poured into a solution of 30 g of NaHCO$_3$ in 800 ml of water with vigorous stirring. The mixture was cooled in ice for 1 hr, and the precipitated solids filtered, washed with water, and air-dried overnight to give 16.7 g of product J, mp 265°-270°.

The acidic filtrates were evaporated almost to dryness under reduced pressure, and the residue dissolved in 30 ml of DMF with heating. The resulting solution was then poured into the preceding NaHCO3 neutralized filtrate with vigorous stirring, and the mixture again chilled in an icebath for one hr. Filtration and air drying of the resulting precipitate furnished an additional 7.0 g of product.

Preparation of 2,6-Dimethyl-1,2,3,4,8,9,1 0, 10a-Octahydronaphth[1,8-cd]azepine-7-ol.

K. 6-Hydroxymethyl-2-Methyl-1,2,3,4,8,9, 10, 10a-Octahydro-naphth[1.8-cd]azepine- 7-ol.

K. 6-Hydroxymethyl-20-Methyl-1,2,3,4,8,9,10,10a-Octahydro-Naphth[1,8-cd]azepine-7-ol.

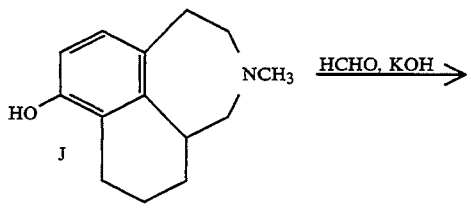

To a solution of 7.0 g of compound J in 125 ml of dimethoXyethane and 125 ml of 3% KOH was adried 9.0 ml of 38% formaldehyde solution. The reaction mixture was heated in an oil bath at 85° with stirring for 40 minutes. It was then cooled to room temperature. and treated dropwise with glacial acetic acid to pH. The mixture was then concentrated to 150 mi, diluted with 100 ml of water, and extracted with two 75 ml portions of methylene chloride. The extracts were combined, dried, and evaporated to dryness. The residue was triturated with a mixture of 1:1 ethanol/acetonitrile and the solids filtered to give 2.2 g of product which was used directly in the next step.

L. 2,6-Dimethyl-1,2,3,4,8,9,1 0,10a-Octahydro-Naphth[1,8. cd]azepine- 7-ol, hydrochloride.

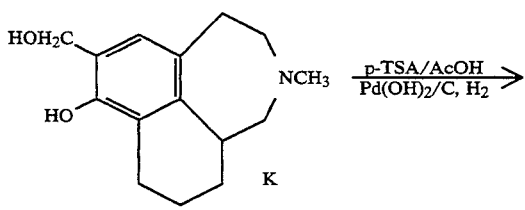

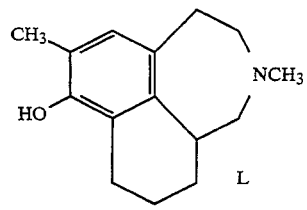

A solution of compound K (2.2 g) and p-toluenesuifonic acid (p-TSA) monohydrate (6.0 g) in 85 ml of glacial acetic acid was hydrogenated over 500 mg of 20% Pd(OH)2 on carbon at 60 psig for 6.5 hrs. The catalyst was then filtered off, the filtrate concentrated to 15 mi under reduced pressure, and adried in small portions with stirring to 250 ml of saturated NaHCO3 solution. The resulting mixture was then extracted with two 75 ml portions of CH2Cl2, and the combined extracts evaporated to dryness to give ca. g of viscous residue. This material was redissolved in ca. 15 ml of CH2Cl2/EtOH (8:2), and chromatographed over 50 g of tic grade silica gel eluting with CH2Cl2EtOH/N-H4OH (50:3:1). Fractions containing the faster-moving component were combined and evaporated to dryness, and the residue digested for a short time with a small amount of CH3CN. On cooling, the material crystallized. This material was converted to the hydrochloride salt by treatment of a CH2Cl2-EtOH solution with ethereal HCI. The crude salt was digested with a 1:1 mixture of EtOAc/EtOH, chilled, and the solid product filtered to give 1.68 g of compound L, mp 275°-280° after drying in vacuum at 80° for 3.5 hrs.

EXAMPLE 3

Preparation of 6-Chloro-2.8.8-Tdmethyl, 1.2.3.4,.8.9.10.10a-Octahydo-Naphth[1,8-cd]azepin-7

M. 6-Chloro-1-(3-methyl-2-butenyl)-2-oxo-3-methyl-7-methoxy-2,3,4,5-tetrahydro-1H -3-benzazepine.

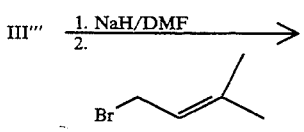

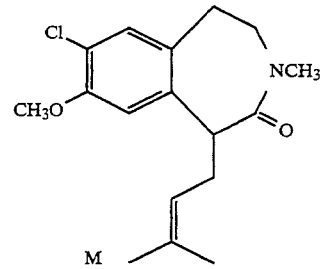

A suspension of NaH (1.92 g, 60% in mineral oil) was adried in small portions to a solution of III" (4.8 g) in a mixture of 35 ml of 1,2-dimethoxyethane and 15 ml of DMF. After 30 min. a solution of 0.022 mole of prenyl bromide in 10 ml of DMF was adried dropwise with stirring. Stirring was continued at 40° for 1.5 hrs, and the reaction mixture then poured into 250 ml of icewater in small portions with vigorous stirring. The precipitated solids were filtered, washed with cold water, and crystallized from acetonitrile to give 2.8 g of product M mp 143°–145°.

N. 6-Chloro- 1 -(3-methyl-2-butenyl)-3-methyl-7-methoxy2,3,4,5-tetrahydro-1 H-3-benzazepine.

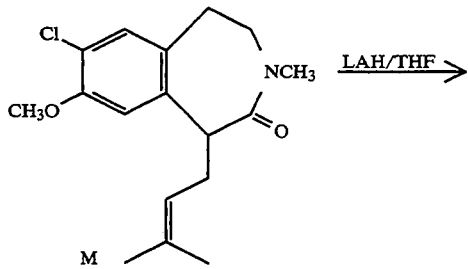

A solution of product M (30.5 g) in 350 ml of dry THF was adried in a rapid dropwise manner to a stirred suspension of LAH4 (10 g) in 200 ml of dry THF. The mixture was stirred at 50° for I hr, then at 40° for another I hr. The cooled and stirred reaction mixture was then treated by the dropwise addition of 10 ml of water, 10ml of 15% NaOH, and finally with another 30 ml of water. The precipitated solids were filtered through Celite, and washed with two 100 ml portions of ether. The combined filtrates were then dried over anhydrous $K_2CO_3$, filtered, and evaporated to dryness to give about 27 g of viscous residue. This material was chromatographed on a column of 400 g of tic grade silica gel, initially eluting with $CH_2Cl_2$/EtOH/$NH_4OH$ (100:3:1), and then with $CH_2Cl_2$/EtOH/$NH_4OH$(50:3:1). Fractions containing the slower moving spot on tic were combined and evaporated in vacuum to give 19.2 g of compound N as a viscous syrup.

0. 6-Chloro- 1 -(3-methyl-2-butenyl)-3-methyl-2,3,4,5-tetrahydro-1 H-3-benzazepin-7-o

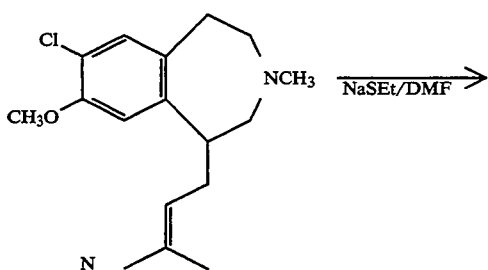

-continued

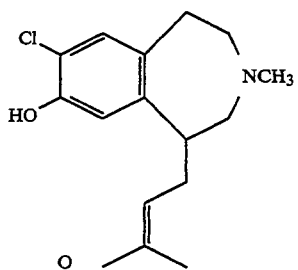

A solution of ethanethiol (12 ml) in 150 ml of DMF was treated portionwise with 7.5 g of 60% NaiI dispersion in mineral oil with stirring. A solution of 19.0 g of product N in 30 ml of DMF was adried to this mixture dropwise with continued stirring. The mixture was blanketed under nitrogen, stirred, and heated at 115° for 3 hrs. After cooling the reaction mixture to 50°, it was poured into 1400 ml of ice-water, and the pH adjusted to ~8 by addition of AcOH. The mixture was extracted with two 200 ml portions of $CH_2Cl_2$, and the combined extracts dried over $MgSO_4$, filtered, and evaporated to dryness to give 18.1 g of viscous syrup. This material was redissoived in 200 ml of $CH_2Cl_2$, and washed with three 400 ml portions of water. The $CH_2Cl_2$ layer was redried over $MgSO_4$, and evaporated to give 15.0 g of compound 0 as a viscous syrup.

P. 6-Chloro-2,8.8-Trimethyl-1,2,3,4,8,9,10,10a-Octahydro-Naphth [1,8-cd]azepin-7-ol.

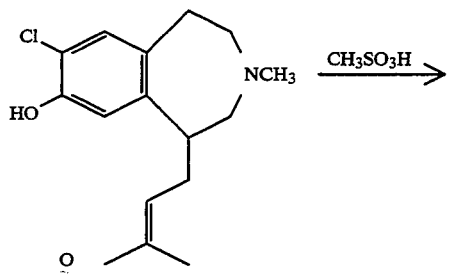

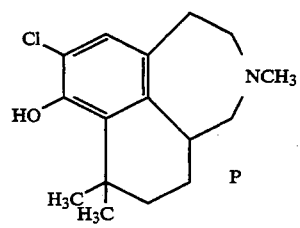

A solution of 400 mg of compound 0 in 8 mi of $CH_3SO_3H$ was stirred at room temperature for two hrs, then poured into 100 ml of water and adjusted to pH 8 by addition of NaOH and finally AcOH. After standing at room temperature overnight, the precipitated solids were filtered, washed with water, and recrystallized from acetonitrile/ethanol (1:1). The solid product was filtered and dried at 80° in vacuo for 6 hrs to give 260 mg of product P mp 217°–219°.

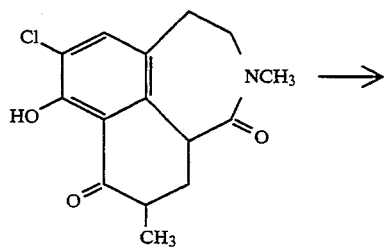

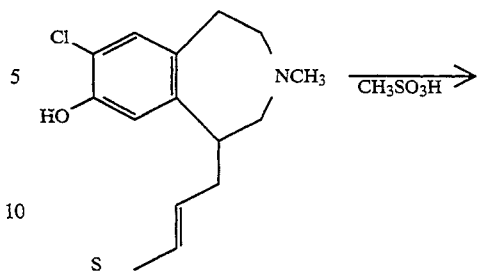

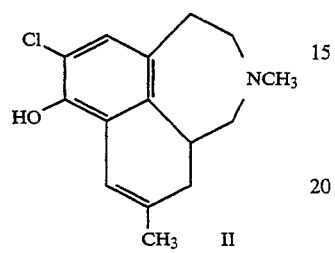

II

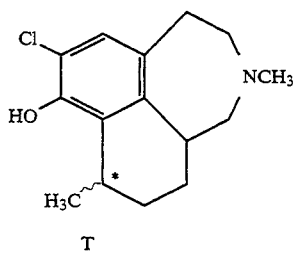

T

Q. A solution of 9.5g of lactam in 125 ml of dry tetrahydrofuran was adried dropwise with cooling and stirring to 100 ml of 1M borane/THF. The mixture was then warmed to room temperature, and heated at reflux overnight. The reaction mixture was evaporated to dryness at 70 degrees under reduced pressure. 40 ml of ethanol was adried to the residue, which was then treated with 40 ml of 20% HCl. The mixture was heated on a steambath for 90 minutes, cooled, organic solvents removed at reduced pressure, and the residue diluted with 150 ml of icewater. The mixture was filtered and treated with small portions of sodium bicarbonate to pH 8. It was extracted with methylene chloride, the extracts dried over magnesium sulfate, filtered, and evaporated to dryness to give 6.5 g of product.

This material was chromatographed over 300 g of silica gel eluting with a mixture of methylene chloride/ethanol/water in the ratio of 100:3:1. Fractions found to contain product via thin-layer chromatography were combined, and evaporated to dryness. Trituration of the residue with acetonitrile resulted in the formation of solids, which were recrystallized from acetonitrile to give 2.2 g of solids which were again recrystallized from ethyl acetate to give 1.1 5 g of material which was rechromatographed on 90 g of silica gel eluting with methylene chloride/ethanol/ammonium hydroxide 50:3:1. Two products were eluted after evaporation of solvents from appropriate fractions. Treatment of the slower eluting product with hot acetonitrile gave the compound of formula II, mp 154–6.

The starting lactam was obtained by procedures analogous to those of example 1 (C) above.

EXAMPLE 4

Preparation of both isomers of 6-chloro-2,8-dimethyl-1.2.3.4.8.9.10.10a-octahydro-naphth [1.8-c.d]azepin-7-ol R. 2.5 g of compound S was cooled in an ice-bath and 50 ml of methanesuifonic acid were adried dropwise. The mixture was stirred at room temperature for 2 hours, then poured into an ice-cooled solution of 30 g NaOH in 300 ml of water. The pH of the solution was then adjusted to about 6 with 50% NaOH, and then to about 8 with NaHCO3. The precipitated solids were filtered and washed with 200 ml of water, then stirred with 100 ml of CH2Cl2 and 300 ml of water to completely dissolve the solids. The water layer was separated, and extracted with two 100 ml portions portions of CH2Cl2, which were combined with the original extract and dried over MgSO4. The mixture was then filtered, and the filtrate evaporated to give a solid residue.This was dissolved in hot ethyl acetate containing a small amount of ethanol, and cooled in the refrigerator overnight.

A crystalline product was filtered from the mixture to give one stereoisomer of compound T, mp 194°–196°. The filtrate was evaporated to dryness, and the solid residue was collected and washed with a small amount of ethyl acetate.This material was then recrystallized from ethyl acetate containing a small amount of ethanol to give a crystalline product mp 179°–181°,o,which was the other stereoisomer of compound T. TheSe compounds are stereoisomers about the position marked with an *. The absolute stereochemical configuration was not assigned to the two stereoisomers that were separated.

Starting material S was prepared according to Scheme 2 in a manner analogous to that described for compound O.

The lefthand column of Table 2 below lists a preparative procedure as described in a particular example. The middle column lists a starting material. The righthand column lists a product. The preparative procedure, starting material, and product in each row of Table 2 below are related. Specifically, by subjecting the listed starting material in a given row to basically the same preparative procedures as are set forth in the listed example of that row, there was obtained the product of that row.

TABLE 2

| Preparative Procedures | Starting material | Product |
|---|---|---|
| Example 2(I) | Cl, HO-substituted tricyclic with NCH₃ | (CH₃)NCO₂-substituted tricyclic with Cl and NCH₃ |
| Example 2(I) | Cl, HO-substituted tricyclic with NCH₃ | 3,5-(CH₃O)₂PhNHCO₂-substituted tricyclic with NCH₃ |
| Example 2(I) | Cl, HO-substituted tricyclic with NCH₃ | 4-iPrPhNHCO₂-substituted tricyclic with NCH₃ and CH₃ |
| Example 2(I) | Cl, HO-substituted tricyclic with NCH₃ | 3,5-(CH₃O)₂PhNHCO₂-substituted tricyclic with NCH₃ and CH₃ |
| Example 3(P) | Cl, HO benzazepine with NCH₃ and CH=CHPh side chain | Cl, HO tricyclic with NCH₃ and Ph |
| Example 3(P) | Cl, HO benzazepine with NCH₃ and CH=CHCH₃ side chain | Cl, HO tricyclic with NCH₃ and CH₃, isomer A |

TABLE 2-continued

| Preparative Procedures | Starting material | Product |
|---|---|---|
| Example 3(P) | [structure: Cl, HO-phenyl fused ring with NCH3 and CH=CH-CH3 substituent] | [structure: Cl, HO-phenyl fused tricyclic with NCH3 and CH3] isomer B |
| Example 1(D) | [structure: Cl, HO-phenyl fused ring with NCH3, C=O, CH3, and ketone] | [structure: Cl, HO-phenyl fused tricyclic with NCH3 and CH3] |
| Example 1(D) | [structure: Cl, HO-phenyl fused ring with NCH3, C=O, and ketone with CH3] | [structure: Cl, HO-phenyl fused tricyclic with NCH3 and CH3] A/B 2:1 |

The following formulations exemplify some of the dosage forms of the compositions of this invention. In each, the term "active compound" refers to the compounds of the formula;

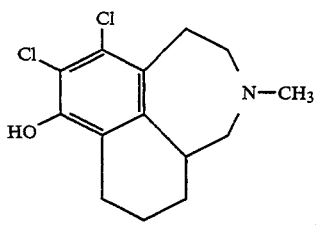

However, this compound may be replaced by equally effective amounts of other compounds of the invention as described above.

EXAMLE A

| | Tablets | | |
|---|---|---|---|
| No. | Ingredients | mg/tablet | mg/tablet |
| 1. | Active compound | 100 | 500 |
| 2. | Lactose NF | 122 | 113 |
| 3. | Corn Starch, Food Grade, as a 10% paste in Purified Water USP | 30 | 40 |
| 4. | Corn Starch, Food Grade | 45 | 40 |
| 5. | Magnesium Stearate NF | 3 | 7 |
| | Total | 300 | 700 |

Method of Manufacture

Mix Item Nos. I and 2 in a suitable mixer for 10-15 minutes. Granulate the mixture with item No. 3. Mill the Hfp granules through a coarse screen (e.g., ¼", 0.63 cm) if necessary. Dry the damp granules. Screen the dried granules if necessary and mix with Item No. 1-4 and mix for 10-15 minutes, Add Item No. 5 and mix for 1-3 minutes. Compress the mixture to appropriate size and weight on a suitable tablet machine.

EXAMPLE B

| | Capsules | | |
|---|---|---|---|
| No. | Ingredient | mg/capsule | mg/capsule |
| 1. | Active compound | 100 | 500 |
| 2. | Lactose NF | 103 | 123 |
| 3. | Corn Starch, Food Grade | 40 | 70 |
| 4. | Magnesium Stearate NF | 7 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

An injectable formulation comprising a compound of the invention may be prepared by using techniques which are conventional in the art.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound having the structural formula

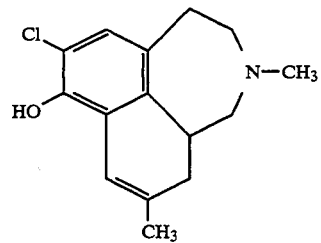

II or a pharmaceutically acceptable salt thereof.

* * * * *